United States Patent [19]

Scholz

[11] 4,233,450

[45] Nov. 11, 1980

[54] PREPARATION OF OXAZOLIDINE-2,4-DIONES

[75] Inventor: Herbert Scholz, Ludwigshafen, Fed. Rep. of Germany

[73] Assignee: BASF Aktiengesellschaft, Fed. Rep. of Germany

[21] Appl. No.: 40,282

[22] Filed: May 18, 1979

[30] Foreign Application Priority Data

Jun. 22, 1978 [DE] Fed. Rep. of Germany ....... 2827414

[51] Int. Cl.³ .......................................... C07D 263/44
[52] U.S. Cl. .................................................... 548/226
[58] Field of Search ......................................... 548/226

[56] References Cited

U.S. PATENT DOCUMENTS

| 2,349,796 | 5/1944 | Stoughton | 548/226 |
| 3,280,136 | 10/1966 | Finkbeiner | 548/226 |
| 3,868,383 | 2/1975 | Hackler | 548/226 |

FOREIGN PATENT DOCUMENTS 729852  1/1943  Fed. Rep. of Germany .

OTHER PUBLICATIONS

Chemical Reviews vol. 58, pp. 71-73, (1958).

*Primary Examiner*—Jose Tovar
*Attorney, Agent, or Firm*—Keil & Witherspoon

[57] ABSTRACT

A novel process for the preparation of oxazolidine-2,4-diones by reaction of ureas with 2-hydroxycarboxylic acid esters.

4 Claims, No Drawings

PREPARATION OF OXAZOLIDINE-2,4-DIONES

The present invention relates to a novel process for the preparation of oxazolidine-2,4-diones by reaction of ureas with 2-hydroxycarboxylic acid esters.

The preparation of oxazolidine-2,4-diones by reacting isocyanates with 2-hydroxycarboxylic acid esters has been disclosed (German Published Appliction DAS 1,811,843, and German Laid-Open Applications DOS 2,022,494 and DOS 2,207,576).

We have found that an oxazolidine-2,4-dione of the formula

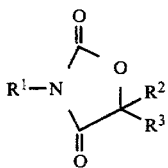

where $R^1$ is aryl of 6 to 12 carbon atoms which is unsubstituted or substituted by one or more halogen atoms, methyl or methoxy, $R^2$ is hydrogen, alkyl of 1 to 4 carbon atoms, methoxymethyl or vinyl and $R^3$ has the same meanings as $R^2$ and in any particular compound $R^2$ and $R^3$ may be identical or different, is obtained in good yield when a urea derivative of the formula

where $R^1$ has the abovementioned meaning and $R^4$ has the same meanings as $R^1$ or is hydrogen, and in any particular compound $R^1$ and $R^4$ may be identical or different, is reacted with a 2-hydroxycarboxylic acid ester of the formula

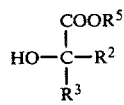

where $R^5$ is alkyl of 1 to 10 carbon atoms or cyclohexyl, and $R^2$ and $R^3$ have the above meanings, at from 100° to 250° C.

The various substituents for example have the following meanings:

$R^1$ and $R^4$ are, for example, phenyl, naphthyl, 2-, 3- and 4-fluorophenyl, 2-, 3- and 4-chlorophenyl, 2-, 3- and 4-bromophenyl, 2,3-dichlorophenyl, 2,3,6-trichlorophenyl, 2-, 3- and 4-methoxphenyl, 2-, 3- and 4-methylphenyl, 3,4-dichlorophenyl, 2,6-dichlorophenyl, 2,3,4-trichlorophenyl, 3,4,5-trichlorophenyl, 2,4,6-trichlorophenyl, 2,3,5-trichlorophenyl and preferably 3,5-dichlorophenyl.

$R^4$ may also be hydrogen.

$R^2$ and $R^3$ are, for example, hydrogen or vinyl or alkyl, eg. methyl, ethyl or methoxymethyl.

$R^5$ is, for example, methyl, ethyl, butyl, isobutyl, isooctyl, nonyl or decyl.

Preferably, $R^1$ and $R^4$ are 3,5-dichlorophenyl, $R^5$ is isobutyl, methyl or butyl, $R^2$ is methyl and $R^3$ is vinyl.

The reaction must be carried out at an elevated temperature, of from 100° to 250° C., preferably from 150° to 240° C.

The reaction can also be carried out in the presence of a trialkylamine, for example tributylamine. This lowers the reaction temperature.

The reaction can be carried out without a solvent. If a solvent is used, it should preferably be one boiling in the above temperature range.

Advantageously, stoichiometric amounts of the starting materials are used for the reaction. However, it is also possible to use an excess, for example of up to 10%, of one of the starting materials, advantageously the cheaper of the starting materials.

To ensure that the reaction gives a good yield, it is important to remove the resulting amines $R^4NH_2$ or $R^1NH_2$ and the resulting alcohol $R^5OH$ virtually quantitatively, preferably by distillation, and to ensure that the 2-hydroxycarboxylic acid ester used as a starting material does not distil with these compounds. The use of packed distillation columns is particularly advantageous for this purpose.

The reaction can be carried out under atmospheric pressure; the use of reduced pressure, of from 5 to 950 mbar, can be of advantage, in order to lower the distillation temperature.

The urea derivatives used as starting materials are obtained, for example, by the conventional reaction of an isocyanate with an amine. For example, reaction of 3,5-dichlorophenyl isocyanate with 3,5-dichloroaniline gives bis-(3,5-dichlorophenyl)-urea (melting point 294° C.).

In view of the known process it is surprising that the process according to the invention takes place in a simple manner and that the end products are obtained in good yield.

The Examples which follow illustrate the process according to the invention.

EXAMPLE 1

A suspension of 210 parts by weight (0.6 mole) of bis-(3,5-dichlorophenyl)-urea and 105.3 parts (0.6 mole) of vinyl-lactic acid isobutyl ester is refluxed for 15 minutes. 19 parts by volume of isobutanol are distilled off through a 40 cm high distillation column of 2 cm diameter, packed with stainless steel wire gauze rings (2,400 meshes/cm²), under atmospheric pressure, the temperature of the mixture being 220°–232° C. and the vapor temperature being 103°–106.5° C. A further 25 parts by volume of isobutanol are then distilled off under a pressure of 200–170 mbar, the temperature of the mixture being 205°–215° C. and the vapor temperature 68.5°–64.5° C. The residue is cooled to 80° C. and 150 parts of methanol are added. The mixture is stirred for a further 2 hours at 20° C. and the solid which has separated out is filtered off and washed with twice 20 parts of methanol.

Yield: 145.6 parts of 3-(3,5-dichlorophenyl)-5-methyl-5-vinyl-1,3-oxazolidine-2,4-dione (=85%). Melting point 101°–104° C.

EXAMPLE 2

A suspension of 175 parts (0.5 mole) of bis-(3,5-dichlorophenyl)-urea in 66.1 parts (0.5 mole) of 2-hydroxyisobutyric acid ethyl ester and 9.3 parts (0.5 mole) of tributylamine is refluxed for 1 hour. 18 parts by volume of ethanol are then distilled off through a distillation column (data as in Example 1) under atmospheric pressure, at a temperature of the mixture of 150°–230° C. and a vapor temperature of 77°–80° C.

The residue is cooled to 50° C. and 150 parts of methanol are added. The mixture is stirred for a further 2 hours at 20° C. and the solid product which has separated out is filtered off and washed with twice 20 parts of methanol.

Yield: 20.1 parts of 3-(3,5-dichlorophenyl)-5,5-dimethyl-1,3-oxazolidine-2,4-dione (=87.6%). Melting point 166°-167° C.

EXAMPLE 3

A suspension of 90 parts (0.5 mole) of 98% pure vinyl-lactic acid isobutyl ester and 102.5 parts (0.5 mole) of N-(3,5-dichlorophenyl)-urea (melting point 190° C.; obtainable, for example, by reacting 3,5-dichlorophenyl isocyanate with ammonia) is refluxed with 11 parts (0.05 mole) of tributylamine for half an hour. 32 parts by volume of distillate are obtained at 150 mbar pressure, the temperature of the mixture being 160°-201° C. and the vapor temperature 68°-86° C. The residue is cooled to 80° C.; 100 parts of methanol are added. The mixture is then stirred for 2 hours at 20° C. and the solid which has separated out is filtered off and washed with twice 20 parts of methanol.

3-(3,5-Dichlorophenyl)-5-methyl-5-vinyl-1,3-oxazolidine-2,4-dione is obtained in somewhat lower yield than described in Example 1. Melting point: 107°-109° C.

We claim:

1. A process for the preparation of an oxazolidine-2,4-dione of the formula

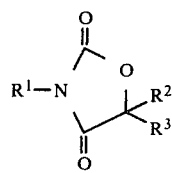

where $R^1$ is aryl of 6 to 12 carbon atoms which is unsubstituted or substituted by one or more halogen atoms, methyl or methoxy, $R^2$ is hydrogen, methoxymethyl, alkyl of 1 to 4 carbon atoms or vinyl and $R^3$ has the same meanings as $R^2$ and in any particular compound $R^2$ and $R^3$ may be identical or different, wherein a urea derivative of the formula

where $R^1$ has the above meanings and $R^4$ has the same meanings as $R^1$ or is hydrogen, and in any particular compound $R^1$ and $R^4$ may be identical or different, is reacted with a 2-hydroxy-carboxylic acid ester of the formula

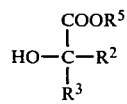

where $R^5$ is alkyl of 1 to 10 carbon atoms or cyclohexyl, at from 100° to 250° C.

2. The process of claim 1, wherein the amines $R^4NH_2$ or $R^1NH_2$ and the alcohol $R^5OH$ formed in the reaction are removed during the reaction.

3. The process of claim 1, wherein the reaction is carried out with a compound in which $R^1$ and $R^4$ denote 3,5-dichlorophenyl, $R^2$ denotes methyl and $R^3$ denotes vinyl.

4. The process of claim 2, wherein the amines and the alcohol are removed in a packed distillation column under conditions such that the 2-hydroxy-carboxylic acid ester is not removed with the amines and alcohol.

* * * * *